(12) United States Patent
Yamamoto

(10) Patent No.: US 10,683,822 B2
(45) Date of Patent: Jun. 16, 2020

(54) FUEL-CETANE-NUMBER ESTIMATION METHOD AND APPARATUS

(71) Applicant: Mitsubishi Heavy Industries, Ltd., Tokyo (JP)

(72) Inventor: Takayuki Yamamoto, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/764,125

(22) PCT Filed: Dec. 11, 2013

(86) PCT No.: PCT/JP2013/083190
§ 371 (c)(1),
(2) Date: Jul. 28, 2015

(87) PCT Pub. No.: WO2014/129049
PCT Pub. Date: Aug. 28, 2014

(65) Prior Publication Data
US 2016/0010580 A1    Jan. 14, 2016

(30) Foreign Application Priority Data
Feb. 22, 2013   (JP) ................................. 2013-033393

(51) Int. Cl.
*F02D 41/14*     (2006.01)
*G01N 33/00*     (2006.01)
(Continued)

(52) U.S. Cl.
CPC ..... *F02D 41/1461* (2013.01); *F02D 41/0025* (2013.01); *F02D 41/401* (2013.01);
(Continued)

(58) Field of Classification Search
None
See application file for complete search history.

(56) References Cited

U.S. PATENT DOCUMENTS

| 5,201,802 A * | 4/1993 | Hirota | ................... F01N 3/2006 60/276 |
| 7,401,591 B2 * | 7/2008 | Yamaguchi | ........... F02D 35/023 123/299 |

(Continued)

FOREIGN PATENT DOCUMENTS

| CN | 101855438 A | 10/2010 |
| EP | 1744040 A1 | 1/2007 |

(Continued)

OTHER PUBLICATIONS

Nanjundaswamy et al., Light-Duty Diesel Engine—Impact of Fuel Properties on Emissions and Performance, FEV Inc., Jun. 4, 2009 (Year: 2009).*

(Continued)

*Primary Examiner* — Jennifer E Simmons
*Assistant Examiner* — Quang X Nguyen
(74) *Attorney, Agent, or Firm* — Berkeley Law & Technology Group, LLP

(57) ABSTRACT

In certain embodiments, a method and an apparatus which can be implemented with a simplified and inexpensive configuration without causing a misfire in a combustion state. In a fuel-Cetane-number estimation method according to embodiments, a map which specifies a relationship between the Cetane number and a control parameter at which NOx concentration of exhaust gas reaches a predetermined value is prepared in advance. Then, the control parameter is controlled variably to detect transition of the NOx concentration of the exhaust gas of the internal combustion engine, and thereby the control parameter of the internal combustion engine at which the NOx concentration has reached the predetermined value is obtained, and the Cetane number which corresponds to the obtained control parameter is estimated on the basis of the map.

14 Claims, 5 Drawing Sheets

(51) Int. Cl.
  *G01N 33/22* (2006.01)
  *F02M 65/00* (2006.01)
  *F02D 41/00* (2006.01)
  *F02D 41/40* (2006.01)

(52) U.S. Cl.
  CPC ......... *F02M 65/00* (2013.01); *G01N 33/0037* (2013.01); *G01N 33/22* (2013.01); *F02D 41/0007* (2013.01); *F02D 41/0072* (2013.01); *F02D 2200/0612* (2013.01); *Y02T 10/44* (2013.01)

(56) References Cited

U.S. PATENT DOCUMENTS

| | | | |
|---|---|---|---|
| 2001/0032457 A1* | 10/2001 | Ludwig | F01N 3/0842 60/285 |
| 2002/0104309 A1 | 8/2002 | Nishiyama et al. | |
| 2007/0092426 A1* | 4/2007 | Driscoll | B01D 53/90 423/352 |
| 2007/0151542 A1 | 7/2007 | Yamaguchi et al. | |
| 2009/0145199 A1* | 6/2009 | Kuronita | G01N 33/2829 73/35.02 |
| 2010/0088008 A1 | 4/2010 | Tanaka et al. | |
| 2011/0168129 A1 | 7/2011 | Kurtz et al. | |

FOREIGN PATENT DOCUMENTS

| | | |
|---|---|---|
| JP | 2002201997 A | 7/2002 |
| JP | 2002256931 A | 9/2002 |
| JP | 2002276345 A | 9/2002 |
| JP | 2007154699 A | 6/2007 |
| JP | 2008082245 A | 4/2008 |
| JP | 2008190403 A | 8/2008 |
| JP | 2008196409 A | 8/2008 |
| JP | 2009144634 A | 7/2009 |
| JP | 2010019115 A | 1/2010 |
| JP | 2010285901 A | 12/2010 |
| JP | 2011117392 A | 6/2011 |
| JP | 2011247214 A | 12/2011 |
| WO | 2009063298 A1 | 5/2009 |
| WO | WO2014129049 A1 | 8/2014 |

OTHER PUBLICATIONS

Notification Concerning Submission, Obtention or Transmittal of Priority Document, App. No. PCT/JP2013/083190, Filed Dec. 11, 2013, dated Feb. 4, 2014, 1 Page.

International Search Report, App. No. PCT/JP2013/083190, Filed Dec. 11, 2013, dated Jan. 14, 2014, 2 Pages.

European Search Report, App. No. 13875644.0, dated Dec. 22, 2015, 9 Pages.

Notification Concerning Transmittal of International Preliminary Report on Patentability, App. No. PCT/JP2013/083190, Filed Dec. 11, 2013, dated Sep. 3, 2015, 14 Pages.

International Search Report, App. No. PCT/JP2013/083190, Filed Dec. 11, 2013, dated Jan. 14, 2014, 11 Pages.

First Office Action, App. No. CN2013800732357, dated Jan. 4, 2017, 22 Pages.

Decision to Grant a Patent, App. No. JP2013-033393, dated Sep. 16, 2016, 6 Pages.

Second Office Action, CN Application No. 201380073235.7, Filed Dec. 11, 2013, dated Jun. 8, 2017, 19 Pages.

Examination Report for Indian App. No. 6670/DELNP/2015, dated May 31, 2019, 7 Pages.

* cited by examiner

OUTPUT ESTIMATION RESULT   ENGINE CONTROL SIGNAL

FUEL-CETANE-NUMBER ESTIMATION METHOD AND APPARATUS

TECHNICAL FIELD

The present invention relates to a fuel-Cetane-number estimation method of estimating a Cetane number of fuel used in a compression ignition type internal combustion engine such as a diesel engine, and an apparatus for implementing the fuel-Cetane-number estimation method.

BACKGROUND

Fuel, such as light oil, is used in a compression ignition type internal combustion engine, such as a diesel engine. However, the Cetane numbers of commercially-supplied fuels are not necessarily constant. Thus, usage of fuel comprising a Cetane number other than a predetermined Cetane number may bring about a misfire and white smoke, as well as an increase in harmful substances contained in exhaust gas, and reduction of the fuel consumption performance. In an approach to solving such a problem, a Cetane number may be estimated for the fuel actually used in an internal combustion engine, and the estimation result may be reflected in the operation control of the internal combustion engine.

There are various methods proposed to estimate a Cetane number of fuel, such as those disclosed in Patent Documents 1 and 2. In Patent Document 1, if an internal combustion engine is in an idle state, a fuel-injection timing appears to be gradually retarded to give rise to a combustion state gradually that is unstable and to deliberately bring about a misfire. In response, the amount of retard at which the misfire occurs is determined, and the Cetane number of the fuel is estimated on the basis of a map that specifies in advance a relationship between the amount of retard and the Cetane number.

In Patent Document 2, a Cetane number appears to be estimated on the basis of a fuel-injection timing at which a relationship "$\Delta P/\Delta CA=a$" is substantially satisfied. $\Delta P$ may correspond to a difference between: an in-cylinder pressure peak value after a top dead center of compression due to combustion brought about by fuel injection; and an in-cylinder pressure peak value of a top dead center of compression or in the vicinity of the same due, at least in part, to combustion responsive to pilot injection before fuel injection or compression of in-cylinder gas due to piston motion. $\Delta CA$ is a difference in crank angles corresponding to the respective in-cylinder pressure values.

Patent Document 1: JP2007-154699A
Patent Document 2: JP2009-144634A

In Patent Document 1, a Cetane number appears to be estimated on the basis of a misfire responsive to in a combustion state by retarding a fuel-injection timing. However, a misfire is a phenomenon that occurs responsive to the combustion state becoming unstable. Further, occurrence of a misfire in a combustion state may lead to a considerable decrease in the fuel consumption performance.

In Patent Document 2, the Cetane number is estimated on the basis of in-cylinder pressure peak values. Thus, it may be necessary to provide an additional in-cylinder pressure sensor in an internal combustion engine to implement the estimation method, which may result in an increase in the implementation cost.

Particular embodiments of claimed subject matter may provide a method and an apparatus for estimating a fuel-Cetane number that can be implemented with a simplified and inexpensive configuration that does not give rise to an unstable combustion state.

SUMMARY

A fuel-Cetane-number estimation method for a fuel used in an internal combustion engine to perform compression ignition combustion may comprise: preparing in advance a map to specify a relationship between the Cetane number of the fuel and a control parameter of the internal combustion engine at which NOx concentration of exhaust gas of the internal combustion engine reaches a predetermined concentration value; controlling the control parameter of the internal combustion engine variably to detect transition of the NOx concentration of the exhaust gas of the internal combustion engine; obtaining the control parameter of the internal combustion engine at which the NOx concentration has reached the predetermined concentration value on the basis of the detected NOx concentration; and estimating the Cetane number which corresponds to the obtained control parameter on the basis of the map.

In another embodiment a Cetane number may be estimated based, at least in part, on a control parameter at which the NOx concentration of the exhaust gas of the internal combustion engine has reached the predetermined value by focusing on the NOx concentration of the exhaust gas which exhibits a change in response to the variable control of the control parameter of the internal combustion engine. A Cetane number may be estimated utilizing a simplified and inexpensive configuration by preparing, in advance, the map which specifies a relationship between the Cetane number of the fuel and the control parameter at which the NOx concentration of the exhaust gas of the internal combustion engine reaches the predetermined concentration value by a method based on a test, an experiment and/or a theory, and applying an actual measurement value of NOx concentration of the exhaust gas to the map.

In an embodiment, fuel-Cetane-number estimation apparatus to estimate a Cetane number of a fuel used in an internal combustion engine which performs compression ignition combustion according to an embodiment includes: a NOx concentration detection unit for detecting NOx concentration of exhaust gas of the internal combustion engine; an internal-combustion-engine control unit for variably controlling a control parameter of the internal combustion engine; a storage unit for storing a map which specifies a relationship between the Cetane number of the fuel and the control parameter of the internal combustion engine at which the NOx concentration of the exhaust gas of the internal combustion engine reaches a predetermined concentration value; and a Cetane-number estimation unit for variably controlling the control parameter with the internal-combustion-engine control unit to vary the NOx concentration of the exhaust gas of the internal combustion engine, obtaining the control parameter at which the NOx concentration reaches the predetermined concentration value, and estimating the Cetane number which corresponds to the obtained control parameter on the basis of the map.

DETAILED DESCRIPTION

Figure 1:
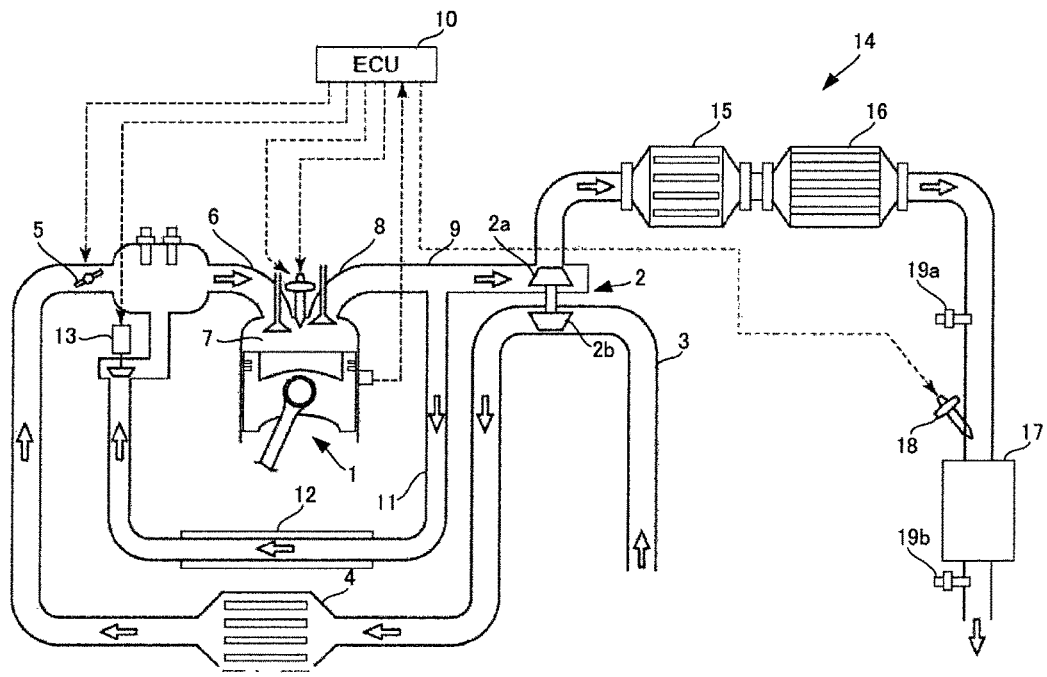
FIG. 1 is a configuration diagram of an overall structure of a fuel-Cetane-number estimation apparatus according an embodiment.

Embodiments of the present invention will now be described in detail with reference to the accompanying drawings. It is intended, however, that unless particularly specified, dimensions, materials, shapes, relative positions and the like of components described in the embodiments shall be interpreted as illustrative only and not limitative claimed subject matter.

A fuel-Cetane-number estimation for a fuel used in an internal combustion engine to perform compression ignition combustion may include preparing in advance a map to specify a relationship between the Cetane number of the fuel and a control parameter of the internal combustion engine at which NOx concentration of exhaust gas of the internal combustion engine reaches a predetermined concentration value. The NOx concentration of the exhaust gas of the internal combustion engine may be affected by a particular state factor (e.g. an engine state or an environmental condition). Thus, accuracy of the map may decrease in accordance with a change in the state factor. In an embodiment, a map may be corrected by a correction value corresponding to a detection result of the state factor, which may permit illumination of influence of a change in the state factor and to estimate a Cetane number accurately under various conditions.

Further, a method may further include: detecting a state factor which affects the NOx concentration of the exhaust gas of the internal combustion engine; and correcting the predetermined concentration value by using a predetermined correction value which corresponds to the detected state factor.

Influence of a change in the state factor can be also reduced by correcting the predetermined concentration value which is used as a standard for determining the NOx concentration. In an embodiment, the predetermined concentration value may be corrected by a correction value corresponding to a detection result of the state factor, which makes it possible to estimate a Cetane number accurately under various conditions.

Specifically, a state factor may include at least one of a temperature of a coolant water, a temperature of an inlet of a cylinder, a pressure of the inlet of the cylinder, oxygen concentration of the cylinder, an amount of intake air, a pressure of the intake air, or a humidity of the intake air of the internal combustion engine.

In an embodiment of the present invention, execution of the fuel-Cetane-number estimation method is started if a predetermined starting condition is satisfied. According to an embodiment, a fuel-Cetane-number estimation method may be executed if a starting condition suitable to execute the control for estimating a Cetane number is satisfied, such as detection of an idling state and detection of operation of an execution button for starting a control by an operator.

A control parameter may comprise an amount of retard in a fuel injection timing in a combustion chamber of the internal combustion engine. Furthermore, a control parameter may comprise an amount of recirculation of the exhaust gas to the intake air of the internal combustion engine.

NOx concentration of the exhaust gas may be affected by an amount of retard of a fuel-injection timing or an amount of recirculation of the exhaust gas to the intake air, which are thus suitable as control parameters for a transition control for estimating a Cetane number.

In an embodiment, fuel-Cetane-number estimation apparatus for estimating a Cetane number of a fuel used in an internal combustion engine which performs compression ignition combustion according to the present invention includes: a NOx concentration detection unit for detecting NOx concentration of exhaust gas of the internal combustion engine; an internal-combustion-engine control unit for variably controlling a control parameter of the internal combustion engine; a storage unit for storing a map which specifies a relationship between the Cetane number of the fuel and the control parameter of the internal combustion engine at which the NOx concentration of the exhaust gas of the internal combustion engine reaches a predetermined concentration value; and a Cetane-number estimation unit for variably controlling the control parameter with the internal-combustion-engine control unit to vary the NOx concentration of the exhaust gas of the internal combustion engine, obtaining the control parameter at which the NOx concentration reaches the predetermined concentration value, and estimating the Cetane number which corresponds to the obtained control parameter on the basis of the map. Accordingly, it is possible to execute a method of estimating a Cetane number of a fuel (including the above embodiments) appropriately.

In one embodiment, a method may further comprise: detecting a state factor, which affects the NOx concentration of the exhaust gas of the internal combustion engine; and correcting the map by using a predetermined correction value which corresponds to the detected state factor.

A fuel-Cetane-number estimation apparatus may include: a state-factor detection unit for detecting a state factor which affects the NOx concentration of the exhaust gas of the internal combustion engine; and a correction unit for correcting the map by using a predetermined correction value which corresponds to the state factor detected by the state-factor detection unit. Accordingly, it is possible to reduce the influence of a change in the state factor and to estimate a Cetane number accurately under various conditions by correcting the map with a correction value corresponding to a detection result of the state factor.

Further a fuel-Cetane-number estimation apparatus may include: a state-factor detection unit for detecting a state factor which affects the NOx concentration of the exhaust gas of the internal combustion engine; and a correction unit for correcting the predetermined concentration value by using a predetermined correction value which corresponds to the state factor detected by the state-factor detection unit. Utilizing a correction unit, it is possible to reduce the influence of a change in the state factor and to estimate a Cetane number accurately under various conditions, by correcting the predetermined value with a correction value corresponding to a detection result of the state factor.

Further, a NOx concentration detection unit may also be used as a NOx sensor to calculate a purification rate in an exhaust-gas purification device for purifying the exhaust gas of the internal combustion engine.

There are an increasing number of vehicles equipped with an exhaust-gas purification device in response to tightening of the exhaust-gas regulations. Exhaust-gas purification device may include a NOx sensor for calculating a purification rate. Thus, using such a NOx sensor also as a NOx concentration detection unit in accordance with certain embodiments may reduce a need to provide an additional sensors or the like, which may be effective in reducing cost.

According to the present invention, it is possible to estimate a Cetane number without bringing about a misfire in a combustion state of an internal combustion engine on the basis of the control parameter at which the NOx concentration of the exhaust gas of the internal combustion engine has reached the predetermined value by focusing on the NOx concentration of the exhaust gas which shows a detectable change in response to the variable control of the control parameter of the internal combustion engine. It is possible to estimate a Cetane number with a relatively simple and inexpensive by preparing in advance a map which specifies a relationship between the Cetane number of the fuel and the control parameter at which the NOx concentration of the exhaust gas of the internal combustion engine reaches the predetermined concentration value by a method based on a test, an experiment or a theory and applying an actual measurement value of NOx concentration of the exhaust gas to the map.

FIG. 1 is a configuration diagram of an overall structure of a fuel-Cetane-number estimation apparatus according to the present embodiment. The reference numeral 1 comprises a diesel engine which is an internal combustion engine including a fuel-injection device of a common-rail type (hereinafter, referred to as an "engine" where appropriate). Fuel is directly injected into a combustion chamber of each cylinder from a fuel injection valve, and thereby compression ignition combustion is performed. The fuel-injection timing and the amount of injection of the fuel injection valves are electrically controlled by an electronic control unit (hereinafter, suitably referred to as "ECU") 10.

The engine 1 includes an exhaust turbine 2a and an exhaust turbocharger 2 having a compressor 2b that is driven coaxially with the exhaust turbine 2a. Air incorporated from an intake pipe 3 is compressed and heated by the compressor 2b, and cooled by an intercooler 4 disposed at the downstream side of the compressor 2b. The supply air cooled by the intercooler 4 is supplied to a combustion chamber 7 via an intake manifold 6.

Compression ignition combustion is performed in the combustion chamber 7, and exhaust gas generated by the combustion is discharged to the outside from an exhaust pipe 9 via an exhaust manifold 8. An exhaust-gas recirculation (EGR) pipe 11 is branched from the exhaust pipe 9 at the upstream side of the exhaust turbine 2a and connected to the intake pipe 3 at the downstream side of a throttle valve 5, so that a part of exhaust gas is re-circulated. An EGR cooler 12 is disposed in the EGR pipe 11, so that the high-temperature exhaust gas is cooled. The amount of recirculation of the EGR gas (EGR amount) is adjusted by the EGR valve 13 disposed in the EGR pipe 11.

The exhaust gas of the engine 1 drives the exhaust turbine 2a disposed in the exhaust pipe 9 to serve as a power source of the compressor 2b, before being supplied to an exhaust aftertreatment system 14. The exhaust aftertreatment system 14 is formed integrally with an oxidation catalyst (DOC) 15 and a diesel particulate filter (DPF) 16. The DOC 15 utilizes oxygen contained in the exhaust gas to oxidize and break down non-combusted substances that mainly contain hydrocarbon (HC) in the exhaust gas into water ($H_2O$) and carbon dioxide ($CO_2$).

The DPF 16 collects particulate matters (PM) contained in the exhaust gas to purify the exhaust gas. If the amount of accumulated PM collected by the DPF 16 increases, the purifying performance decreases. Thus, regeneration process is performed on the DPF 16 at a predetermined timing. If the DPF 16 is regenerated, the DOC 15 at the upstream side oxidizes fuel in the exhaust gas to heat the exhaust gas, and the exhaust gas having a high temperature is supplied to the DPF 16, thereby combusting the accumulated PM.

In the exhaust pipe 9 at the downstream side of the exhaust aftertreatment system 14, disposed is a NOx selective catalytic reduction (SCR) 17 (hereinafter, referred to as "denitration catalyst") for decomposing nitrogen oxide (NOx) in the exhaust gas into water ($H_2O$) and nitrogen ($N_2$). A urea injection nozzle 18 for spraying urea solution, which is a reductant, into the exhaust pipe 9 is disposed at the upstream side of the denitration catalyst 17.

If the urea solution is sprayed to the exhaust gas, ammonia is produced from the urea solution by hydrolysis as shown in the following formula (1).

$$(NH2)_2CO + H_2O \rightarrow CO_2 + 2NH_3 \quad (1)$$

Further, the denitration reaction between the ammonia ($NH_3$) and the nitrogen oxide (NOx) at the denitration catalyst 17 is varied depending on the reaction rate, taking place according to one of the following formulas (2) to (4).

$$4NH_3 + 4NO + O \rightarrow 4N_2 + 6H_2O \quad (2)$$

$$2NH_3 + NO + NO_2 \rightarrow 2N_2 + 3H_2O \quad (3)$$

$$8NH_3 + 6NO_2 \rightarrow 7N_2 + 12H_2O \quad (4)$$

The ECU 10 obtains detection values of NOx sensors 19a and 19b disposed at the upstream side and the downstream side of the denitration catalyst 17, calculates the NOx purification rate at the denitration catalyst 17, and performs various controls such as a control of the additive amount of the urea solution on the basis of the calculation result. For instance, the ECU 10 obtains a target NOx purification rate on the basis of the operation state (such as an engine load and a rotation speed) of the engine 1 and the catalyst temperature of the denitration catalyst 17, and compares the target NOx purification rate to an actual NOx purification rate calculated on the basis of detection values detected by the NOx sensors 19a and 19b, so as to control the additive amount of reductant or the timing to start addition.

In the present embodiment, in addition to the above general control, the ECU 10 achieves efficient operation by estimating a Cetane number of fuel used in the engine 1, and reflecting the estimation result on a normal operation control (e.g. by performing correction based on the estimation results on engine-control parameters in a normal operation such as a fuel-injection control parameter, an EGR control parameter, and a variable-turbo control parameter). Specifically, the ECU 10 functions as an arithmetic unit for implementing the method of estimating a Cetane number according to the present invention.

The NOx concentration of the exhaust gas of the internal combustion engine may be affected by a particular state factor (e.g. an engine state or an environmental condition). Thus, accuracy of the map may decrease in accordance with a change in the state factor. In the present embodiment, the map is corrected by a correction value corresponding to a detection result of the state factor, which makes it possible to reduce the influence of a change in the state factor and to estimate a Cetane number accurately under various conditions.

Figure 2:
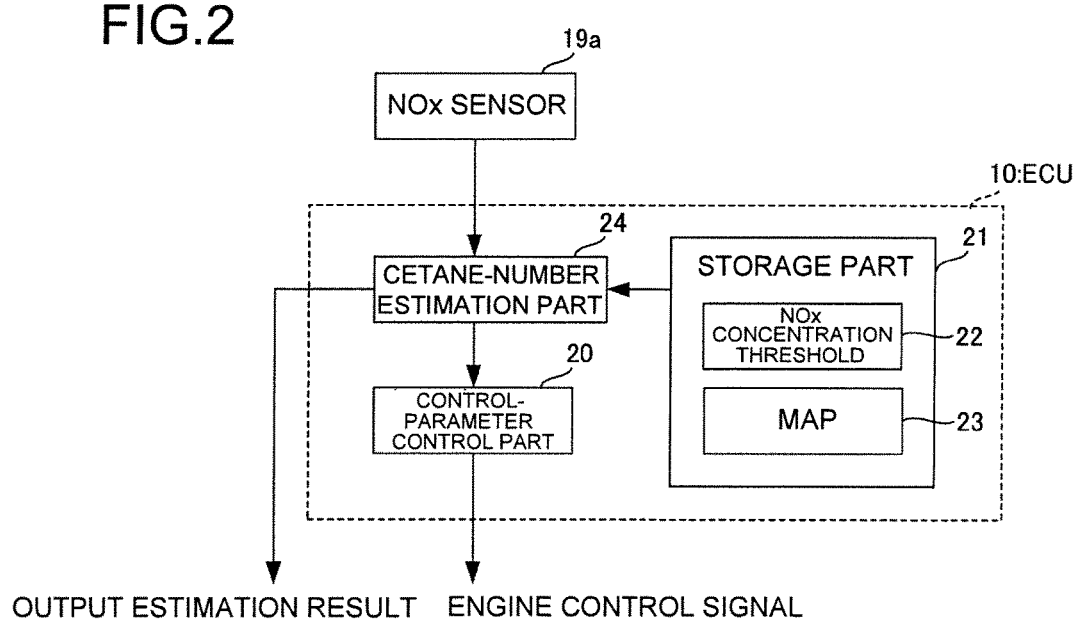
FIG. 2 is a conceptual diagram of an interior configuration of ECU illustrated as function blocks for implementing a method of estimating a fuel-Cetane-number according to an embodiment.

FIG. 2 is a conceptual diagram of an interior configuration of the ECU 10 illustrated as function blocks for implementing a method of estimating a fuel-Cetane-number.

A control-parameter control part 20 performs a variable control on a control parameter of the engine 1 by transmitting control signals. The control parameters to be controlled may comprise parameters related to an operation state of the engine 1 and capable of affecting the NOx concentration in the exhaust gas. Preferably, the amount of retard of the fuel-injection timing or the EGR amount may be used as the control parameters. The series of fuel-Cetane-number estimation controls described below can be applied regardless of the type of control parameters. Hereinafter, to make it easier to understand, the controls will be described in detail with reference to a case where the amount of retard of the fuel-injection timing is used as a control parameter.

Figure 3:
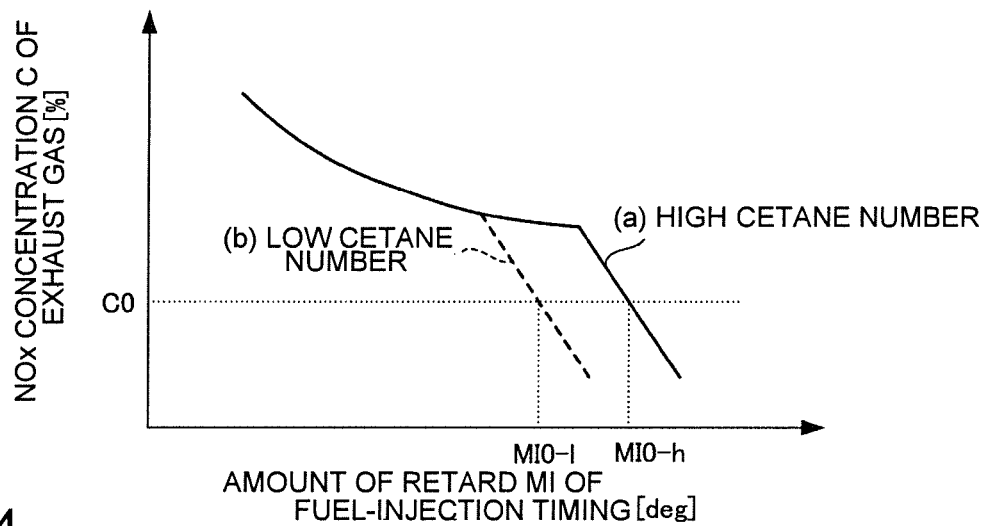
FIG. 3 is a graph showing a change in NOx concentration of exhaust gas in a case where the amount of retard of a fuel-injection timing is controlled according to an embodiment.

Here, FIG. 3 is a graph showing a change in NOx concentration of exhaust gas in a case where the amount of retard MI of a fuel-injection timing is controlled variably. The horizontal axis is the amount of retard MI of the fuel-injection timing, and the vertical axis is the NOx concentration C of exhaust gas. Further, in FIG. 3, the solid line (a) represents the characteristic of a fuel having a higher Cetane number, while the dotted line (b) represents the characteristic of a fuel having a lower Cetane number.

The graph shows a trend that, if the amount of retard MI of the fuel injection timing is gradually increased, the combustion state of the engine 1 gradually becomes unstable, and the NOx concentration C of exhaust gas decreases. In the characteristic graph, the slope of the amount of retard MI becomes steep across a predetermined value, and the decreasing speed of NOx concentration increases. The amount of retard at which the slope becomes steep depends on the Cetane number. As illustrated in FIG. 3, the slope changes rapidly at a smaller amount of retard in the characteristic graph (b) having a lower Cetane number than in the characteristic graph (a) having a higher Cetane number.

A storage part 21 of the ECU 10 stores in advance a NOx-concentration threshold value C0 (reference numeral 22 in FIG. 2) which is information required to estimate a Cetane number, and a map 23. FIG. 3 illustrates an example of the NOx-concentration threshold value C0 stored in the storage part 21. The NOx-concentration threshold value C0 is set so as to cross lines in a region of the characteristic graph where the slope rapidly changes.

Here, the amount of retard at which a line in the characteristic graph crosses the NOx-concentration threshold value C0 is defined as MI0. In the example of FIG. 3, the retard amount MI0 of the lines (a), (b) in the characteristic graph is respectively MI0-$h$ and MI0-1. The amount of retard MI0 depends on the Cetane number of fuel used in the engine 1. The map 23 specifies the correlation between the amount of retard MI0 and the Cetane number.

Figure 4:
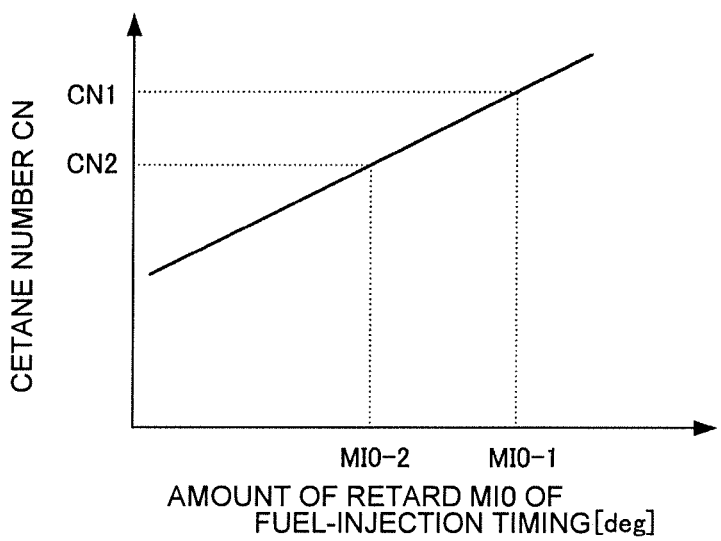
FIG. 4 is an example of a map that specifies a correlation between the amount of retard and the Cetane number of fuel used in an engine according to an embodiment.

Here, FIG. 4 is an example of a map 23 which specifies a correlation between the amount of retard MI0 and the Cetane number CN of fuel used in an engine. According to the map 23, the Cetane numbers corresponding to the amounts of retard MI0-$h$ and MI0-1 illustrated in FIG. 3 are estimated to comprise respectively CN 1 and CN 2.

As illustrated in FIG. 2, a Cetane-number estimation part 24 of the ECU 10 determines the NOx concentration of the exhaust gas by obtaining a detection value detected by the NOx sensor 19a at the upstream side, and estimates a Cetane number by the above process on the basis of the NOx concentration threshold value C0 and the map 23 read out from the storage part 21.

Figure 5:
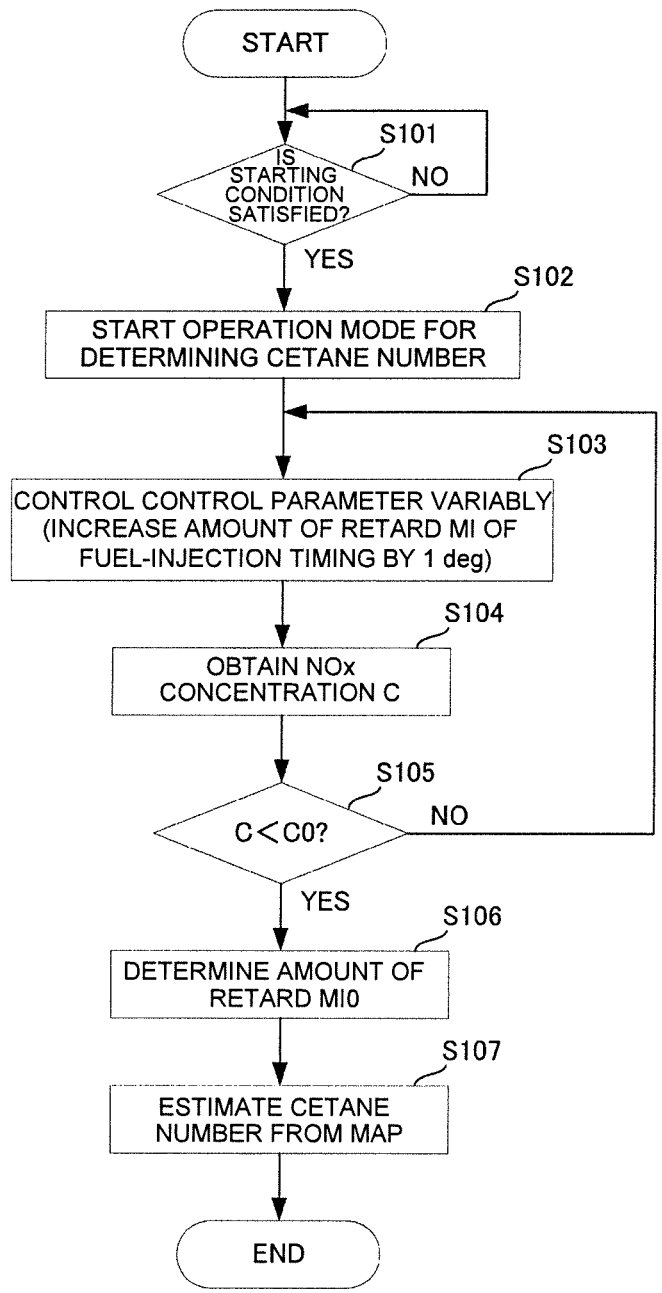
FIG. 5 is a flowchart of control operation of a fuel-Cetane-number estimation apparatus according to the present embodiment according to an embodiment.

With reference to FIG. 5, the control operation of the fuel-Cetane-number estimation device according to the present embodiment will be described in sequence.

FIG. 5 is a flowchart of control operation of a fuel-Cetane-number estimation apparatus according to the present embodiment.

First, under a condition in which the engine 1 is in normal operation, the ECU 10 determines whether a predetermined starting condition is satisfied (step S101). If the starting condition is satisfied (step S101: YES), the ECU 10 starts a Cetane-number determination operation mode to execute estimation of a Cetane number of fuel according to the procedures described below (step S102).

Here, the starting condition is a trigger condition for starting the Cetane-number determination operation mode. For instance, it is determined whether a condition suitable to execute controls for estimating a Cetane number is satisfied, such as detection of an idling state and detection of operation of an execution button for starting a control by an operator.

To mention a specific example, in a case where determination is performed on the basis of an idling state, it is possible to execute the Cetane number estimation under a condition in which the operation state of the engine is stable by starting the Cetane number determination operation mode if the idling state has lasted for a predetermined period, which makes it possible to obtain good estimation accuracy.

Further, if determination is performed on the basis of detection of operation of an execution button, it is possible to start the Cetane number determination operation mode at an optional timing intended by an operator (mainly a driver). Thus, it is possible to prevent a driver from being disturbed by the Cetane-number determination operation mode starting at a unintended timing.

In another example of the starting condition, the Cetane-number estimation may be executed without user input by detecting replenishment operation if a fuel tank is replenished with additional fuel. In this case, the Cetane number of stored fuel may change due to the additional fuel supplied to the fuel tank. Thus, it is possible to control the engine suitably by executing the Cetane-number determination operation mode to re-evaluate an accurate Cetane number and reflect the accurate Cetane number on the operation control.

Once the Cetane-number determination operation mode is started, the state ECU 10 transmits a control signal to the engine 1 from the control parameter control part 20 to control the control parameters variably (step S103). In step S103, the control parameter control part 20 variably controls the amount of retard to increase by 1 degree, and then the ECU 10 obtains the NOx concentration C of exhaust gas on the basis of the detection value detected by the NOx sensor 19 (step S104). Then, the ECU 10 determines whether the NOx concentration C obtained in step S104 is smaller than the NOx concentration threshold value C0 obtained from the storage part 21 (step S105). If the NOx concentration C is not less than the NOx concentration threshold value C0 (step S105: NO), the ECU 10 returns the process to step S103, and increases the amount of retard MI by another 1 degree.

While increasing the amount of retard MI by 1 degree every time as described above, the process is repeated until the NOx concentration C of exhaust gas becomes smaller than the NOx concentration threshold value C0. Then, once the NOx concentration C becomes smaller than the NOx concentration threshold value C0 (step S105: YES), the ECU 10 determines the amount of retard at this time as MI0 (step S106). Specifically, the ECU 10 specifies the amount of retard MI0 at the time if the NOx concentration C reaches the NOx concentration threshold value C0 by obtaining the NOx concentration C of exhaust gas while variably controlling the amount of retard MI of the amount of fuel injection.

If the amount of retard MI of the fuel injection timing is increased, the combustion state gradually becomes unstable, and a misfire occurs eventually. However, the range in which the control parameters are variably controlled in step S103 is within a range in which a misfire does not occur. That is, in the present embodiment, it is possible to evaluate a Cetane number on the basis of the NOx concentration at the time if the control parameters are variably controlled in a range where a misfire does not occur.

Subsequently, the ECU 10 estimates the Cetane number by applying the amount of retard MI0 obtained in step S106 to the map 23 (step S107). As descried above, in the map 23 prepared in advance in the storage part 21, a relationship between the amount of retard MI0 and the Cetane number CN is specified in advance, and the ECU 10 applies the amount of retard MI0 obtained in steps S106 to the map 23 to obtain the corresponding Cetane number CN as an estimation value.

As described above, it is possible to estimate a Cetane number without causing a misfire in the combustion state of the engine 1, by controlling the control parameters of the engine 1 variably and using the control parameter MI0 of the time if the NOx concentration C of exhaust gas has reached the predetermined concentration value C0. In particular, the map 23 specifying a relationship between the Cetane number CN and the control parameter MI0 of the time if the NOx concentration C of exhaust gas reaches a predetermined concentration value C0 is prepared in advance by a method based on a test, an experiment or a theory, which makes it possible to estimate a Cetane number with a simplified and inexpensive configuration by applying the actual measurement value of the NOx concentration of exhaust gas to the map.

Further, the NOx concentration used to estimate a Cetane number is obtained on the basis of the detection value detected by the NOx sensor 19a, while the NOx sensor 19a is also used to calculate the purification rate of the denitration catalyst 17. Thus, it is possible to estimate a Cetane number without providing an additional sensor or the like, and thus the present embodiment is advantageous in terms of cost as well.

Although the fuel injection timing is selected as a control parameter in a substantial part of the above description, the EGR amount or the like may be used as a control parameter. Also in this case, it is possible to estimate the Cetane number by a similar method by evaluating the NOx concentration of exhaust gas if the EGR amount is controlled variably.

In an embodiment, a Cetane number of fuel is estimated on the basis of the map 23 specifying a relationship between a Cetane number CN of fuel and a control parameter MI0 at the time if the NOx concentration C of exhaust gas reaches a predetermined concentration value C0 set in advance. According to the research of the present inventors, the relationship specified in the map 23 as described above is affected by state factors that affect the NOx concentration of exhaust gas (e.g. the temperature of the coolant water for the engine, the temperature of a cylinder inlet, the pressure of the cylinder inlet, the oxygen concentration of the cylinder inlet, the amount of intake air, the pressure of the intake air, and the humidity of the intake air).

While an example of the map 23 is illustrated in FIG. 4, the relationship in the drawing is specified for a case in which the engine 1 has constant state factors. If the state factors change, there is a problem that an error in the map 23 increases and the accuracy in estimating a Cetane number decreases. In the modified embodiment 1, to solve the above problem, the map 23 is corrected in accordance with the state factors of the engine 1, which makes it possible to improve the accuracy in estimating a Cetane number.

Figure 6:
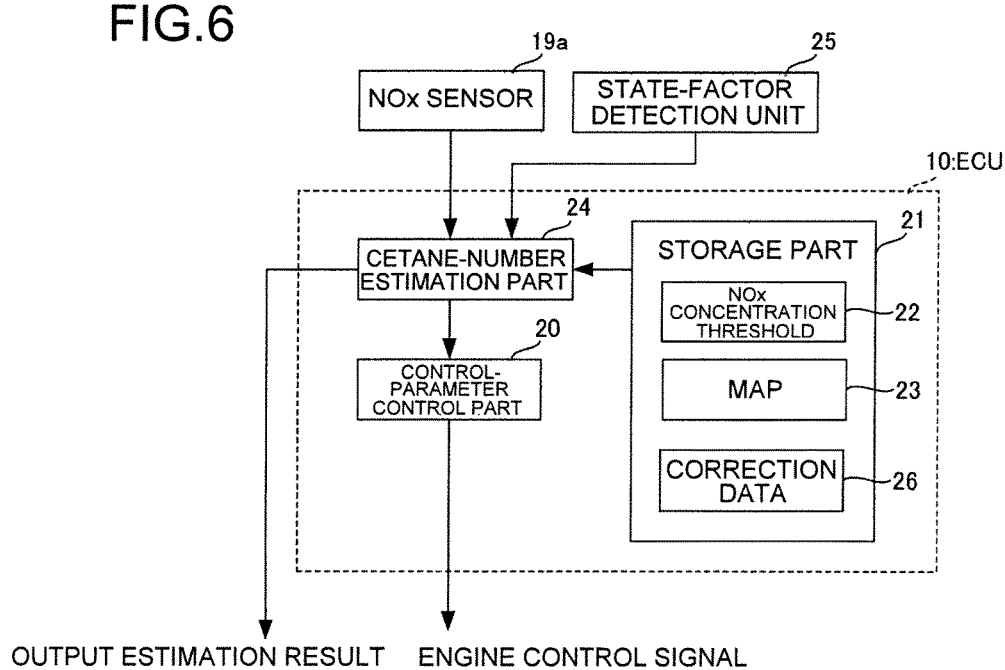
FIG. 6 is a conceptual diagram of an interior configuration of ECU, illustrated as function blocks for implementing the method of estimating a fuel-Cetane-number according to an embodiment.

FIG. 6 is a conceptual diagram of an interior configuration of the ECU 10 according to the first modified embodiment, illustrated as function blocks for implementing the method of estimating a fuel-Cetane-number. Here, elements similar to those in the above embodiment are indicated by the same reference numerals, and not described in detail again.

The state factor of the engine 1 is detected by a state-factor detection unit 25, and monitored by a Cetane-number estimation unit 24. Here, the state-factor detection unit 25 is a plurality of sensors corresponding to the types of the state factors. Further, the storage part 21 stores collection data 26 which specifies correction values for correcting the map 23, and the detection value of the state-factor detection unit 25 is associated with a correction value corresponding to the detection value in a form of a map.

The Cetane-number estimation part 24 calculates a correction value corresponding to the detection value obtained from the state-factor detection unit 25 on the basis of the correction data 26, and corrects the map 23.

Figure 7:
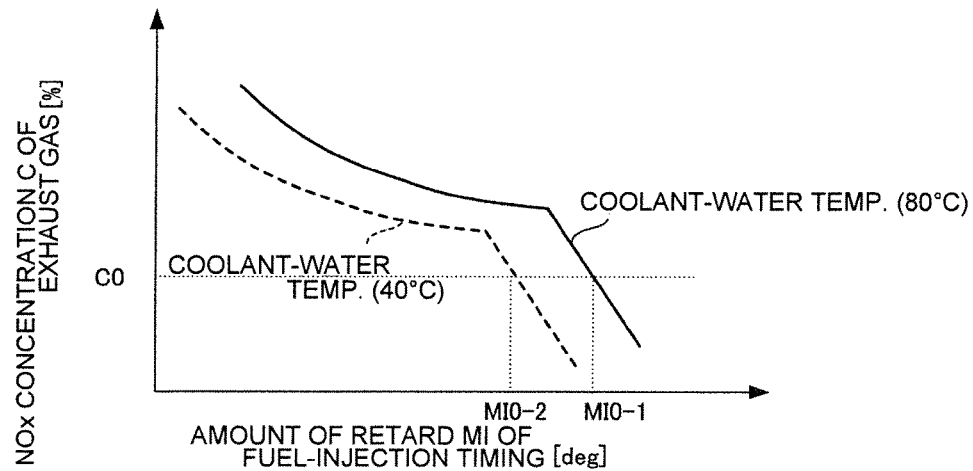
FIG. 7 is a graph of relationships between a control parameter and NOx concentration of exhaust gas at different coolant-water temperatures, for an engine using a fuel having the same Cetane number according to an embodiment.

Here, with reference to FIG. 7, the effect of the coolant-water temperature T of the engine 1 being an example of the state factors will be examined. FIG. 7 is a graph of relationships between a control parameter and NOx concentration of exhaust gas at different coolant-water temperatures, for an engine using a fuel having the same Cetane number. The temperature of the coolant water is 80° C. in the solid line, and 40° C. in the dotted line.

In comparison of the lines, if the coolant-water temperature T is lower, the NOx concentration C of exhaust gas starts to decrease at a smaller amount of retard MI. Thus, there are two different parameters MI0 that cross the NOx concentration threshold value C0 depending on the temperature: MI0-1 and MI0-2. As described above, the control parameters MI being a standard of estimation of a Cetane number are dispersed. Thus, if a Cetane number were obtained without correcting the map 23, the estimate value would vary even though the same fuel is used.

Figure 8:
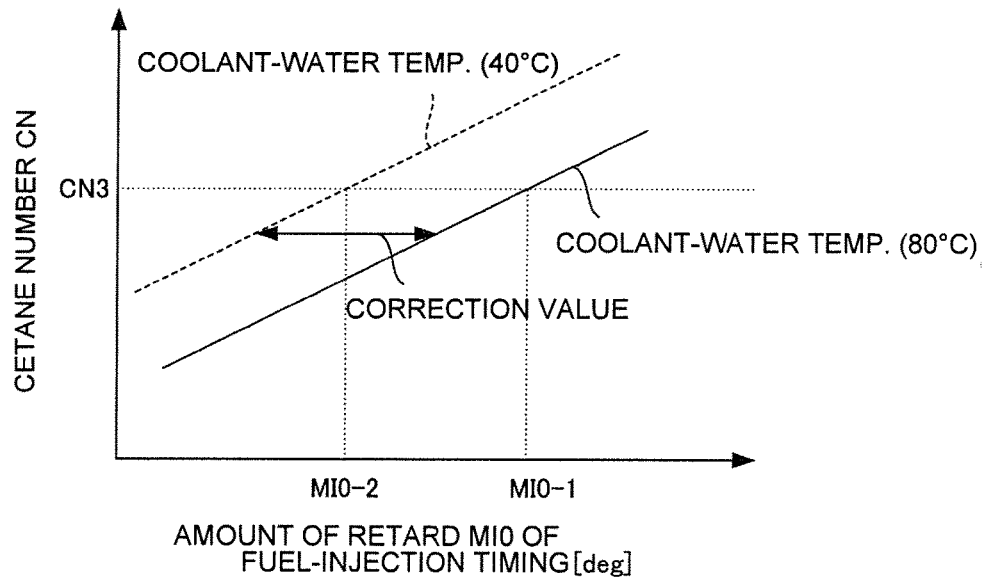
FIG. 8 is a map including the amount of correction according to an embodiment.

In view of this, a correction value corresponding to the temperature of the coolant water is specified in the correction data 26 to correct the map 23 so that the dispersion of estimation results due to the difference in the temperature of the coolant water becomes zero. Specifically, the difference in the characteristic graph between different temperatures of the coolant water is accumulated in the correction data 26 in advance as correction values as illustrated in FIG. 8, and a correction value corresponding to the detection value detected by the state-factor detection unit 25 (a coolant-water thermometer in this case) is read out, thereby correcting the map 23. As a result, it is possible to match the estimation value of the Cetane number corresponding to each of the control parameters MI0-1 and MI0-2 to an accurate value CN3.

In the first modified embodiment, the map 23 is corrected in accordance with the state factors, which makes it possible to estimate a Cetane number accurately under various conditions. Here, the accuracy in estimating a Cetane number can be improved on the basis of a similar technical idea also in a case where the temperature of the cylinder inlet, the pressure of the cylinder inlet, the oxygen concentration of the cylinder inlet, the amount of intake air, the pressure of the intake air, the humidity of the intake air or the like is used as a state factor instead of the temperature of the coolant water of the engine 1. Specifically, possible errors that occur in the map 23 if the above factors are varied are accumulated as correction values in the correction data 26, and a corresponding correction value is read out from the correction data 26 on the basis of the actual measurement value measured by a corresponding sensor or the like to correct the map 23, which makes it possible to improve the accuracy in estimating a Cetane number.

In an embodiment, a correction value for the map 23 may be specified as the correction data 26 to reduce an influence of a change in the state factors. On the other hand, the second modified embodiment is different in that the correction value corresponding to the NOx concentration threshold value NOx0 is specified as the correction data 26 to eliminate an influence of a change in the state factor. Here, elements similar to those in the above embodiment are indicated by the same reference numerals, and not described again in detail.

Figure 9:
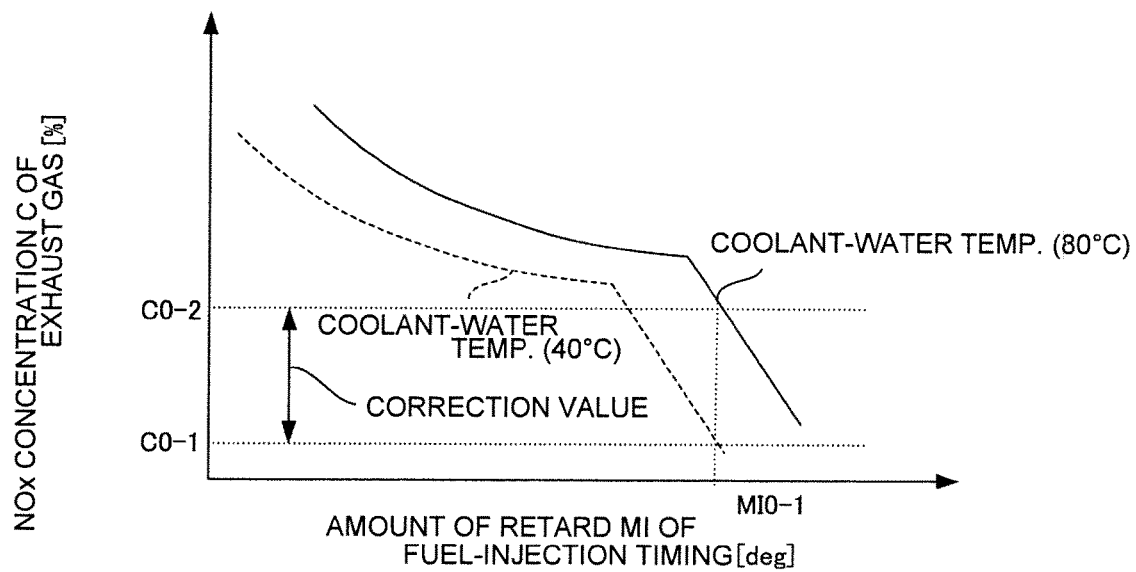
FIG. 9 is a characteristic graph including the amount of correction according to an embodiment.

FIG. 9 is a graph of relationships between a control parameter (the amount of retard MI) and NOx concentration C of exhaust gas at different coolant-water temperatures, for an engine 1 using fuel having the same Cetane number, like FIG. 7. The temperature of the coolant water is 80° C. in the solid line, and 40° C. in the dotted line. As described above, if a Cetane number is estimated on the basis of a constant NOx concentration threshold value C0, there is an error in the characteristic graph due to the temperature of the coolant water, and the amount of retard MI0 at which the NOx concentration reaches the NOx concentration threshold value C0 is also dispersed (see FIG. 7). Thus, a Cetane number cannot be estimated accurately.

In view of this, as illustrated in FIG. 9, a correction value is set so that the amount of retard MI0 at which the NOx concentration reaches the NOx concentration threshold value C0 stays consistent regardless of the temperature of the coolant water, and the NOx concentration threshold value corresponds to the temperature of the coolant water. The correction value is associated with the temperature of the coolant water and accumulated in the correction data 26 stored in the storage part, similarly to the first modified embodiment.

In FIG. 9, the correction value is set such that the NOx concentration threshold value is C0-1 in a case where the temperature of the coolant water is 80° C., and the NOx concentration threshold value is C0-2 in a case where the temperature of the coolant water is 40° C. In this way, the NOx concentration threshold value is corrected so that the amounts of retard MI0 at which the NOx concentration reaches the NOx concentration threshold value are consistent.

In an embodiment, the NOx concentration threshold value is corrected in accordance with the state factors, which makes it possible to estimate a Cetane number accurately under various conditions.

The invention claimed is:

1. A method of estimating a Cetane number of a fuel to be used in an internal combustion engine to perform compression ignition combustion, comprising:
   preparing a map to indicate a relationship between the Cetane number of the fuel and an amount of retard in a fuel injection timing in a combustion chamber of the internal combustion engine at which NOx concentration of exhaust gas of the internal combustion engine reaches a threshold concentration;
   preparing a characteristic graph showing a change in a NOx concentration of the exhaust gas in a case where the amount of retard is controlled variably for a plurality of Cetane numbers;
   detecting the NOx concentration;
   controlling the amount of retard of the internal combustion engine to detect transition of the NOx concentration of the exhaust gas of the internal combustion engine;
   obtaining the amount of retard of the internal combustion engine at which the NOx concentration has reached the threshold concentration, based, at least in part, on the detected NOx concentration; and
   estimating the Cetane number to correspond to the obtained amount of retard, based on the map,
   wherein the NOx concentration with respect to the amount of retard has a first region where the slope gradually decreases and a second region where the slope rapidly decreases,
   the amount of retard in the second region is greater than the amount of retard in the first region, and
   wherein the threshold concentration is set to cross lines in a region of the characteristic graph where the NOx concentration is smaller than a value at which the slope of the NOx concentration with respect to the amount of retard rapidly changes in each of the plurality of Cetane numbers as in the second region.

2. The method according to claim 1, further comprising:
   detecting a state factor to affect the NOx concentration of the exhaust gas of the internal combustion engine; and
   correcting the map by using a correction value to correspond to the detected state factor.

3. The method according to claim 2,
   wherein the state factor includes a temperature of a coolant water, a temperature of an inlet of a cylinder, a pressure of the inlet of the cylinder, oxygen concentration of the cylinder, an amount of intake air, a pressure of the intake air, or a humidity of the intake air of the internal combustion engine, or any combination thereof.

4. The method according to claim 1, further comprising:
   detecting a state factor to affect the NOx concentration of the exhaust gas of the internal combustion engine; and
   correcting a predetermined concentration value by using a threshold correction value to correspond to the detected state factor.

5. The method according to claim 4,
   wherein the state factor includes a temperature of a coolant water, a temperature of an inlet of a cylinder, a pressure of the inlet of the cylinder, oxygen concentration of the cylinder, an amount of intake air, a pressure of the intake air, or a humidity of the intake air of the internal combustion engine or any combination thereof.

6. The method according to claim 1, wherein the method is started without user input if the fuel is supplied to a fuel tank.

7. The method according to claim 1, wherein the method is started without user input when an idling state has lasted for a predetermined period.

8. The method according to claim 1, wherein the method is started without user input when operation of an execution button for starting a control by an operator is detected.

9. An apparatus for estimating a Cetane number of a fuel, the fuel to be used in an internal combustion engine to perform compression ignition combustion, comprising:
   a NOx concentration detection unit to detect NOx concentration of exhaust gas of the internal combustion engine;
   an internal-combustion-engine control unit for varying an amount of retard in a fuel injection timing in a combustion chamber of the internal combustion engine;
   a storage unit for storing a map to specify a relationship between the Cetane number of the fuel and the amount of retard of the internal combustion engine at which the NOx concentration of the exhaust gas of the internal combustion engine reaches a threshold concentration and a characteristic graph showing a change in the NOx concentration of the exhaust gas in a case where the amount of retard is controlled variably for a plurality of Cetane numbers; and
   a Cetane-number estimation unit for varying the amount of retard with the internal-combustion-engine control unit to vary the NOx concentration of the exhaust gas of the internal combustion engine, obtaining the amount of retard at which the NOx concentration reaches the threshold concentration, and estimating the Cetane number to correspond to the obtained amount of retard, based on the map;
   wherein the NOx concentration with respect to the amount of retard has a first region where the slope gradually decreases and a second region where the slope rapidly decreases,
   the amount of retard in the second region is greater than the amount of retard in the first region, and
   wherein the threshold concentration is set to cross lines in a region of the characteristic graph where the NOx concentration is smaller than a value at which the slope of the NOx concentration with respect to the amount of retard rapidly changes in each of the plurality of Cetane numbers as in the second region.

10. The apparatus according to claim 9, further comprising:
    a state-factor detection unit to detect a state factor to affect the NOx concentration of the exhaust gas of the internal combustion engine; and
    a correction unit to correct the map by using a correction value to correspond to the state factor detected by the state-factor detection unit.

11. The apparatus according to claim 9, further comprising:
    a state-factor detection unit to detect a state factor to affect the NOx concentration of the exhaust gas of the internal combustion engine; and
    a correction unit to correct the threshold concentration by using a correction value which corresponds to the state factor detected by the state-factor detection unit.

12. The apparatus according to claim 9, wherein the NOx concentration detection unit is also used as a NOx sensor to calculate a purification rate in an exhaust-gas purification device for purifying the exhaust gas of the internal combustion engine.

13. The apparatus according to claim 9, wherein the internal combustion engine control unit varies the amount of retard when an idling state has lasted for a predetermined period.

14. The apparatus according to claim 9, wherein the internal combustion engine control unit varies the amount of retard when operation of an execution button for starting a control by an operator is detected.

* * * * *